US007720524B2

(12) United States Patent  (10) Patent No.: US 7,720,524 B2
Srinivas et al.  (45) Date of Patent: May 18, 2010

(54) METHOD, APPARATUS, AND SYSTEM FOR DETECTING DISEASE STATES IN A LIVING BODY USING A GAMMA RAY COUNTER

(76) Inventors: Shyam Mohan Srinivas, 28640 Blue Pond Trail, Solon, OH (US) 44139; Richard Kon Yoon, 18931 Kinbrace St., Northridge, CA (US) 91326

( * ) Notice: Subject to any disclaimer, the term of this patent is extended or adjusted under 35 U.S.C. 154(b) by 697 days.

(21) Appl. No.: 11/428,560

(22) Filed: Jul. 4, 2006

(65) Prior Publication Data

US 2008/0021256 A1   Jan. 24, 2008

(51) Int. Cl.
*A61B 6/00* (2006.01)
(52) U.S. Cl. ....................................................... 600/436
(58) Field of Classification Search ............... 600/3, 600/436
See application file for complete search history.

(56) References Cited

U.S. PATENT DOCUMENTS

| | | | | |
|---|---|---|---|---|
| 6,091,070 A * | 7/2000 | Lingren et al. | ......... | 250/370.09 |
| 6,587,710 B1 * | 7/2003 | Wainer | ......................... | 600/427 |
| 6,650,930 B2 * | 11/2003 | Ding | .......................... | 600/436 |
| 6,810,281 B2 * | 10/2004 | Brock et al. | ................. | 600/427 |
| 2002/0054853 A1 * | 5/2002 | Linder et al. | ................ | 424/9.36 |
| 2003/0179853 A1 * | 9/2003 | Amemiya et al. | .............. | 378/63 |

OTHER PUBLICATIONS

Yasuhisa et al, Copper-62-ATSM: A New Hypoxia Imaging Agent with High Membrane Permeability and Low Redox Potential, The Journal of Nuclear Medicine, 1997, vol. 38 No. 7, pp. 1155-1160.*

* cited by examiner

*Primary Examiner*—Eric F Winakur
*Assistant Examiner*—Saurel J Selkin
(74) *Attorney, Agent, or Firm*—Richard Yoon

(57) ABSTRACT

A method and system of detecting a disease state in a targeted organ is described using nuclear medicine techniques. In preferred embodiments, a radiotracer with specific uptake for diseased portions of the targeted organ is administered to a patient. A gamma ray counter with at least one gamma ray detector is used to count gamma rays emitted by the radiotracer. By placing the gamma ray detector over the location of the targeted organ, the gamma ray counter can provide a quick yes or no answer on whether the disease state exists in the targeted organ.

29 Claims, 4 Drawing Sheets

METHOD, APPARATUS, AND SYSTEM FOR DETECTING DISEASE STATES IN A LIVING BODY USING A GAMMA RAY COUNTER

FIELD OF THE INVENTION

This invention relates to systems used in nuclear medicine (or molecular imaging) and more specifically to the use of gamma counting technology to detect disease states in a living body.

BACKGROUND OF THE INVENTION

It is estimated that there are 95,000,000 emergency room visits in one year in the United States. Of these approximately 8,000,000 (8.4%) of these are patients complaining of chest pain. This puts the onus of ruling out a myocardial infarction (MI), commonly known as a "heart attack," on the emergency room physician. Because of the potential seriousness of this condition, it is essential that the emergency room physician accurately determine whether the etiology of the chest pain is cardiac in nature. Given the state of medical liability in the United States, unless the doctor can clearly rule out an MI, current medical practice is to subject them to at least a 24-hour hospital admission. During the hospital admission, typically three sets of blood tests are performed 8 hours apart looking for the leakage of cardiac enzymes indicating myocardial injury. If any one of these blood tests returns a positive result, the patient is deemed to have had an MI, and then further workup and treatment is pursued. However, as a result of this practice, from these 8 million patients complaining of chest pains about 4.8 million (60%) are admitted. However, the vast majority of these patients do not have a cardiac etiology for their chest pain, as a mere 104,000 (1.3%) patients actually are having an MI. Often emergency room visits result in unnecessary hospital admissions. In an effort to reduce needless hospital admissions and the costs associated with them, and to give the appropriate treatment for patients in an expeditious manner, a more effective method of screening for patients with acute coronary syndromes is desirable.

SUMMARY OF THE DISCLOSURE

A method and system of detecting a disease state in a targeted organ is described using nuclear medicine techniques. In preferred embodiments, a radiotracer with specific uptake for diseased portions of the targeted organ is administered to the patient. A gamma ray counter with at least one gamma ray detector is used to count gamma rays emitted by a single photon radiotracer. By placing the gamma ray detector over the location of the targeted organ, the operator of the gamma ray counter can determine if the disease state exists in the targeted organ based on whether a "hot spot" is detected by the gamma ray counter. In specific embodiments, the hot spot from a focal collection of a positron emitting radiotracer is detected using two gamma ray detectors placed in front and back of the targeted organ. A coincidence counter is used in conjunction with the gamma ray detectors to determine the presence or absence of the positron tracer in the targeted organ. In the preferred embodiments, the gamma ray counter provides a yes or no answer on whether the disease state exists in the targeted organ.

In a specific embodiment, the targeted organ is the heart and the disease state that is being diagnosed is an acute coronary syndrome that can lead to a myocardial infarction. For detecting acute coronary syndromes, the present invention describes using a radiotracer that detects the presence of hypoxic myocardium and in particular embodiments uses a specialized thiosemicarbazone radiotracer such as $^{62}$Cu-ATSM or one of the many nitroimidazole derivatives that exist for this purpose.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
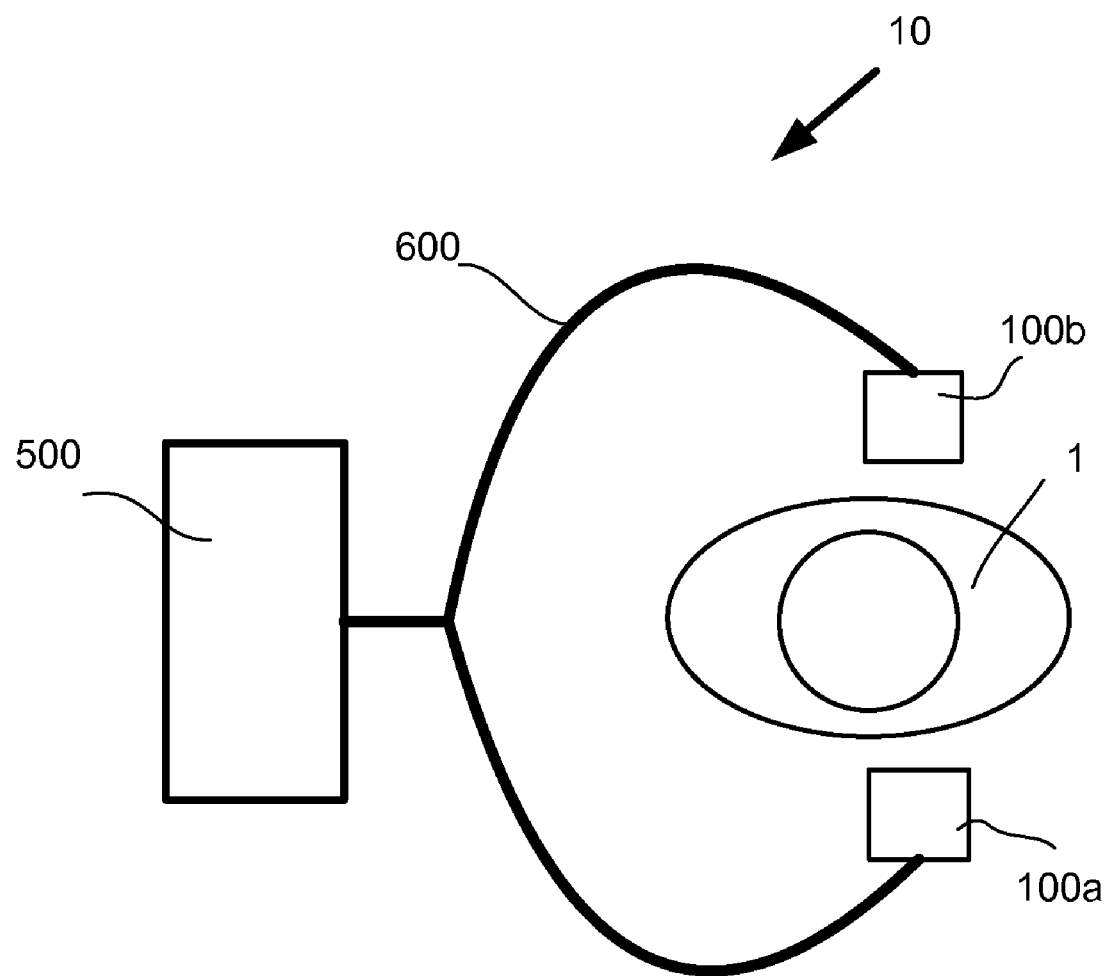
FIG. 1 is a top view of the gamma ray counter in accordance with a preferred embodiment of the present invention.

As shown in the drawings for purposes of illustration, the invention is embodied in a medical device which can detect disease states using nuclear medicine techniques. In preferred embodiments of the present invention, the medical device is used to quickly triage whether a patient is experiencing an acute coronary syndrome (ACS) and help expedite therapy to prevent an MI. However, it will be recognized that further embodiments of the invention may be used to determine other disease states quickly. In preferred embodiments, the present invention attempts to tackle the diagnosis of an ACS by providing a simple yes/no answer. However, alternative embodiments may attempt to provide additional imaging of the heart to provide additional information to the physician.

Myocardial perfusion imaging (MPI) is the current method by which cardiac perfusion is assessed using nuclear imaging techniques. Although MPI is not conventionally used with the chest pain patient, it is more recently being used in conjunction with the blood tests to diagnose suspected acute coronary syndromes. A likely scenario in the emergency room is that the emergency room doctor will refer the admitted patient for MPI while the patient waits for his blood tests. SPECT ("Single Photon Emission Computed Tomography") or PET ("Positron Emission Tomography") imaging is performed by injecting the patient with radioisotopes that have a rapid clearance from the blood and high myocardial extraction. Commonly used SPECT radiotracers are Tl-201 Chloride, Tc-99m Sestamibi, and Tc-99m Tetrofosmin. PET utilizing Rb-82 Chloride or N-13 Ammonia has also recently become an established method used for diagnosis and prognostication in patients with suspected acute coronary syndromes. The MPI technique relies on the presence of a perfusion defect that is visualized as a "cold spot" on the images. This principle requires that the tracer should be administered at the time of the ischemia and the perfusion defect should be large enough to be resolved with the current SPECT or PET instrumentation.

However, limitations exist with MPI imaging at the diagnosis stage. First of all, many community based hospitals do not even have SPECT or PET cameras. Usually major university hospitals or highly funded private hospitals will have access to these imaging devices due to their high price. In addition, because of the high cost of SPECT and PET devices, costs to perform these tests are very high for the payors of the procedure. Furthermore, current methods using conventional MPI result in delays of diagnosis for the patients, as tests are usually completed after several hours. In addition, it requires the skilled manpower of nuclear medicine technologists and physicians to perform, read, and interpret the study, making it both expensive and time consuming. In addition, given that a great majority of the patients admitted with chest pains do not have acute coronary syndromes, many patients are subject to high doses of radiation unnecessarily.

Figure 2:
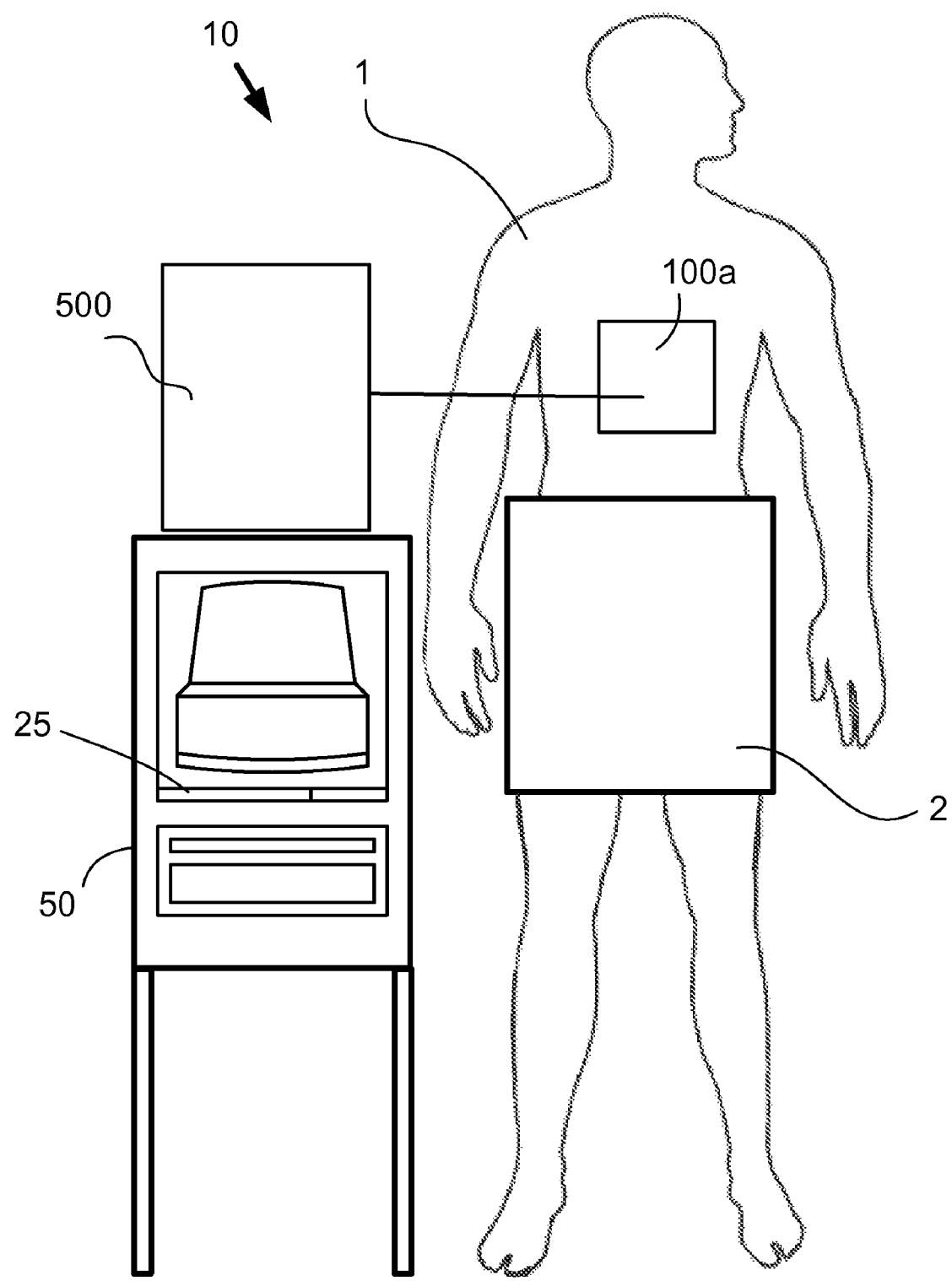
FIG. 2 is a front view of the gamma ray counter as shown in FIG. 1.

In accordance with a preferred embodiment of the present invention, a different approach is used to detect the presence of myocardial ischemia compared to the MPI approach. In the preferred embodiments, different types of tracers are used that will be taken up by the ischemic or hypoxic myocardium and would result in a "hot spot" in the traditional sense of nuclear medicine. In other words, tracers are selected that will be trapped by non-oxygenated parts of the heart (i.e. hypoxic tissue) rather than tracers that have uptake in healthy tissue. The advantage of such an approach is that the entire heart need not be imaged to see if there are "cold" perfusion defects within the heart, but the simple detection of a "hot spot" will indicate the presence of hypoxia secondary to an acute coronary syndrome. In converse, the absence of a "hot spot" will show that the patient is not suffering from an acute coronary syndrome. In accordance with the preferred embodiment, such a procedure would avoid the need for imaging (and the high cost of imaging equipment), and could simply provide a yes or no answer based on a gamma ray counter 10 as shown in FIGS. 1 and 2, which will be described in detail below. Furthermore, if myocardial changes are present far beyond that of the actual flow abnormality, the detection of an ACS could be obtained after the ischemic episode, taking advantage of the phenomenon of "ischemic memory" where metabolic changes to the cell are prolonged and last longer than the period of transient hypoxia. Thus, in accordance with the preferred embodiments, the gamma ray counter 10 works to identify either the presence or absence of hypoxic myocardium in patients with a suspected acute coronary syndrome (that may progress to an MI). This gamma ray counter 10 can potentially be operated in the emergency room, as the counter 10 is designed to be portable, and a nuclear medicine technologist could perform the test himself/herself. Interpretation is a yes or no answer based on the number of counts revealed by the gamma ray counter 10. This could also be easily determined by the emergency room physician himself/herself, making diagnosis of an acute coronary syndrome into no more than a 5 minute procedure. There will be much less in terms of manufacturing cost for this device as compared to the large current day SPECT and PET scanners, which translates to a smaller charge for the test itself. The ease of use, combined with the time savings to both hospital staff and the patient make it an attractive option for diagnosis. A further object of the invention is to reduce the dose of radioactive material administered to a patient. In the preferred embodiments, only 5 mCi of radiotracer would be needed to be administered versus approximately 8 times that amount currently used for MPI (5 mCi as opposed to nearly 40 mCi) which results in less ionizing radiation exposure to the patient. More or less radiotracer can be administered to the patient in accordance with the preferred embodiments (e.g. 2 to 12 mCi, but preferably between 5 to 10 mCi), yet less than 15 mCi to 40 mCi used in other PET or SPECT procedures. Thus, the objectives of the present invention are to enhance patient safety, expedite the care of the patient if he/she is having angina of cardiac etiology, and allow the normal patient to be sent home—a clear advantage for both the physician and patient.

18-Fluorodeoxyglucose (FDG) is probably the most available commercial tracer that can be used to detect the metabolism changes that occur in the hypoxic heart. In the past, an off-label use of FDG was to assess the post ischemic metabolic changes related to stress induced ischemia. However, the applicability of the FDG tracer for the present described method has not been established for use in the heart. A more specific radiopharmaceutical to trace hypoxia may result in a more accurate technique to diagnose the presence of an acute coronary syndrome. In accordance with the preferred embodiments, a relatively new hypoxia radiotracer known as copper-62 labeled thiosemicarbazone ($^{62}$Cu-ATSM) has been effective in extracting this type of physiological information. This tracer is a positron emitter that has the property of being trapped by cells that have an overabundance of reducing power in their mitochondria due to a lack of oxygen. The fast kinetics of this thiosemicarbazone makes this an ideal tracer to identify tissue that is transiently hypoxic. Ability to detect the presence of hypoxic myocardium using a hypoxic radiotracer in combination with the gamma ray counter 10 of FIGS. 1 and 2 provides a more effective triage for the acute coronary syndrome patient. In alternative embodiments, other hypoxia tracers that uses either a single photon or positron emitting nuclides can be employed since any of them could be detected by the gamma ray counter 10. Alternative hypoxia tracers from the nitroimidazole class (as opposed to thiosemicarbazone like ATSM) include: 18F-EF5, 18F-FMISO, 18F-FRP170, 18F-FAZA, and 123I-IAZA. These 2-nitroimidazole derivatives with specific uptake for hypoxic tissue may also be used to detect hypoxic myocardium using the gamma ray counter 10.

In accordance with alternative embodiments of the present invention, through the use of other specific radiotracers, this gamma ray counter 10 of FIGS. 1 and 2 could potentially provide vital functional information for patients with other disease states. For example, a patient with a solitary pulmonary nodule discovered on a chest x-ray or CT scan often needs to know if the lesion needs to be biopsied or not. This could be accomplished with injection of the patient with FDG and the presence or absence of gamma ray counts as determined by the device would help triage this patient. Other scenarios which take advantage of radiotracers for specific disease states could also potentially benefit from determining the presence of binding using the gamma ray counter 10 of FIGS. 1 & 2. In further alternative embodiments, another use of the gamma counter 10 is as a portable imaging device for ICU patients with a fever of unknown origin ("FUO"), who often are too unstable to be transported to a nuclear medicine department. Being able to localize a source of gamma counts in either the thorax, abdomen, pelvis, or extremity (as in a vascular graft) using the tracers In-111, Tc-99m labeled white blood cells, or FDG will help narrow down the source of infection. Such a counter could potentially be used as well, when the mere presence or absence of activity makes a diagnostic difference, as in a brain death scan.

FIGS. 1 & 2 illustrate the gamma ray counter 10 being used on a patient 1 in a top view (FIG. 1) and front view (FIG. 2) respectively in accordance with the preferred embodiments of the present invention. In preferred embodiments, the gamma ray counter 10 is comprised of two detectors 100a and 100b, arms 600, and a processing unit 500. The detectors 100a and 100b are used to count the gamma photons which are emitted from the specific targeted area of a patient body 1 after a tracer is administered to the patient 1, as described above. The specific workings of the detectors 100a and 100b will be discussed in more detail with respect to FIG. 3. In FIGS. 1 and 2, according to the preferred embodiments, the detectors 100a and 100b are positioned over the heart of patient 1 to detect acute coronary syndromes using the $^{62}$Cu-ATSM or other hypoxia radiotracer. In preferred embodiments, the detectors 100a and 100b are 4 to 6 inch$^3$ cubes for placement in front and back of the heart as seen in FIG. 1. Cube shaped detectors are preferred for ease of manufacturing and the small size of the detectors will limit the cost of the material needed to build the detectors. For example, the crystal used to detect the gamma rays are often the most expensive part of today's PET cameras and by limiting the size of the detector, huge cost savings can be made in the manufacture of the gamma ray counter 10. However, the detectors 100a and 100b can be manufactured in various sizes and shapes. For example, the detectors 100a and 100b may be rectangular, triangular, oval shaped, etc. In addition, the detectors can be made smaller or larger. For example, if the detectors 100a and 100b are used to detect gamma photons emitted from the lung, the size might be 1 foot in height and 1-2 feet in length. Moreover, the detectors 100a and 100b do not have to be identical in shape and size, but merely in function. In further alternative embodiments, the detectors 100a and 100b can be replaced with more than two detectors or even a single detector. For example, the detectors 100a and 100b can be replaced by a large annular detector where the body is placed through the central bore of a ring (similar to today's PET or CT scanners), or if the tracer is a single photon emitter, a single detector that simply counts events can be used.

The arms 600 contain electrical connections that deliver signals registered by the detectors 100a and 100b to the processing unit 500. In preferred embodiments, the electrical connections are formed from electrical wires within the arms 600 that will transmit the signals from the amplification electronics of both detectors 100a and 100b to the processing unit 500. In addition, according to the preferred embodiments, the exterior of the arms 600 will be made of a segmented flexible material such that they allow for ease of positioning in front of and behind the patient 1. The arms 600 will be flexible enough to be adjusted by the operator of the gamma ray detector 10 but hold position once the detectors 100a and 100b are placed in proper position (similar to a dentist light in a dental office or a gooseneck desklamp on a desk). In preferred embodiments, the arms will be about 4 to 5 feet in length, but any size or shape is possible. In further alternative embodiments, the arms may be made solid with additional latitude and longitude mechanisms to allow for placement of the detectors 100a and 100b in the proper location. In addition, although FIGS. 1 and 2 show how the gamma ray counter 10 is used on a patient that is standing up, alternative embodiments of the gamma ray counter can be used while the patient is sitting down in a chair/stool or lying down on a table. If a table (not shown) is used, the table itself can be a detector or a thin table can be made from a carbon polymer based material which will have low gamma ray attenuation such that the second detector can be placed beneath the table. It is also possible to use a single detector with a patient lying down on a table.

As seen in FIG. 2, an apron 2 is used to cover a part of the patient 1 when operating the gamma ray detector 10. In preferred embodiments, apron 2 is a ½" thick lead apron around the abdomen that will help attenuate background gamma photons which may accumulate in the liver, kidneys, or in other visceral organs due to normal physiologic distribution of the radiotracer.

According to preferred embodiments, the processing unit 500 shown in FIGS. 1 & 2 contain the electronics to control (i.e. turn on/off, set settings, etc.), receive and process the signals from the detectors 100a and 100b, and calculate the result of the gamma ray detector 10. Details of the processing unit 500 will be discussed with respect to FIG. 4. In the preferred embodiments, the processing unit 500 is connected to a computer 25, which is used to program the settings of the gamma ray detector 10 and display the result of the gamma ray detector 10. In FIG. 2, the processing unit 500 is shown as being placed on a stand 50, which also stores the computer 25. However, in alternative embodiments, the input, computing, and display elements of the computer 25 may be embodied in the processing unit 500 so to make the processing unit 500 a stand alone unit. The processing unit 500 can also be situated directly on the floor, or attached to a wall. In further embodiments, the processing unit 500 can be networked to a central server or another computer that is located at a different location where both controls and display may be inputted or sent to another location.

Figure 3:
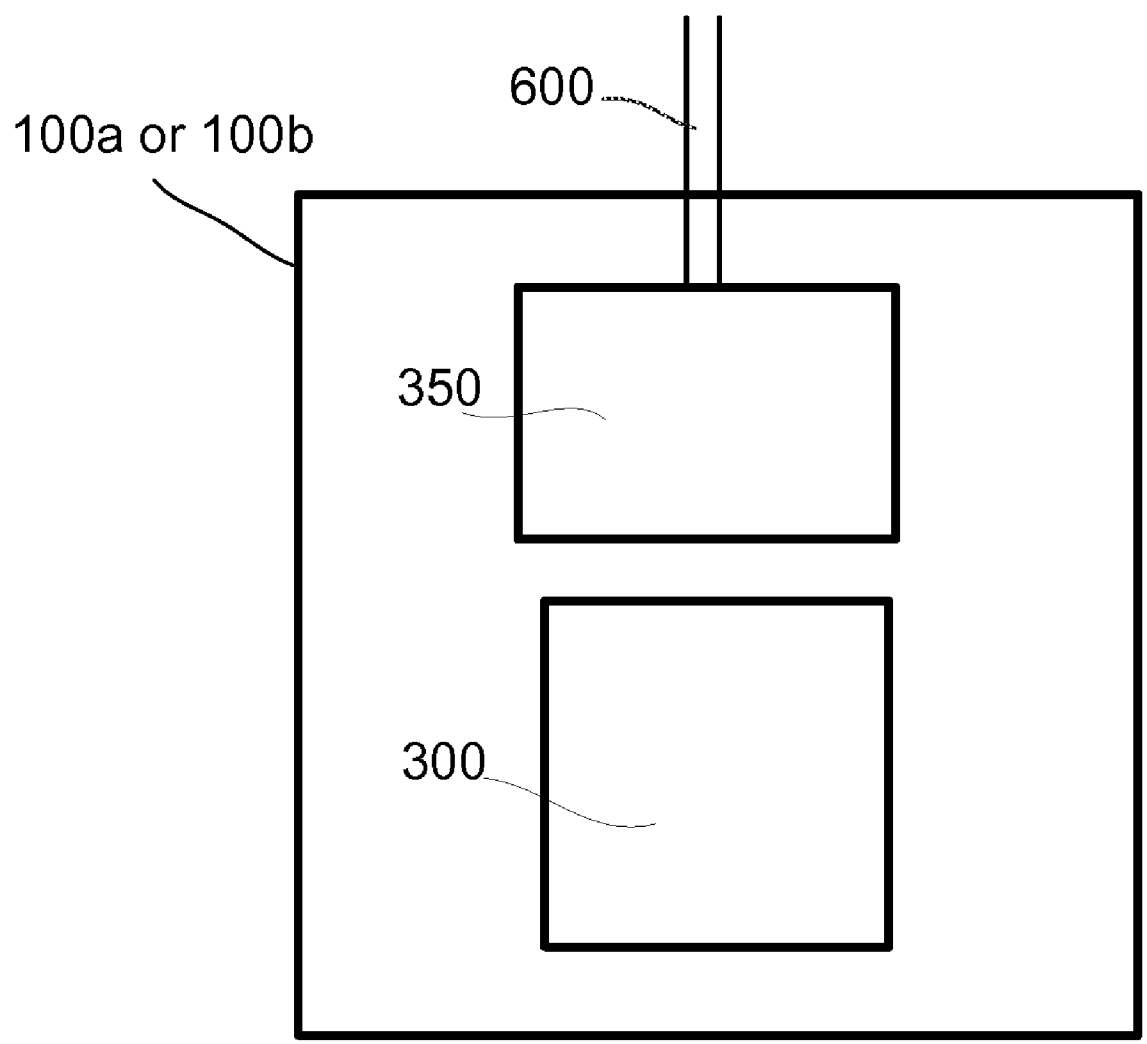
FIG. 3 is a schematic top view of the detector used with the gamma ray counter in FIGS. 1 and 2.

FIG. 3 is a schematic top view of the detector 100a or 100b used with the gamma ray counter 10 in FIGS. 1 and 2. The detectors 100a and 100b each have two key components, a gamma ray sensor 300 and an amplifier 350. The gamma ray sensor 300 is located on the side that will be placed closest to the patient 1. In preferred embodiments, the sensor 300 will contain 1 cm$^3$ of semiconductor material such as Cadmium-Zinc-Telluride (CZT) which has the ability to convert 511 keV (or lower) gamma photons into an electrical signal. The semiconductor photodetectors such as CZT have p-doped and n-doped materials that are juxtaposed creating an inherent electrical field within the material. This electrical field results in a "depletion region" where electron-hole pairs that are generated from photon absorption within the semiconductor are swept to either sides of the material and produce a current. The current is proportional to the number of photons that interact with the semiconductor. In addition, although 1 cm$^3$ of semiconductor material is considered to be sufficient to meet the needs of detecting positrons emitted by the $^{62}$Cu-ATSM or other hypoxia tracer from the heart, more or less semiconductor material can be used within the detectors 100a and 100b. In addition, although the preferred shape of the semiconductor material is a cube, the semiconductor material can be made of different proportions and shapes. In alternative embodiments, other material can be used which have similar abilities to convert gamma rays into an electrical signal. Another potential semiconductor material is Cadmium-Telluride (CdTe), a proportional gas filled chamber is also a possibility, or alternatively the more traditional scintillator crystals could be used. For example, 1 cm$^3$ of scintillator crystal (such as LYSO) could be used to convert gamma photons into secondary photons.

In preferred embodiments, the amplifier 350 is located behind the sensor 300 and will contain amplification electronics that will receive the signals from the CZT semiconductors and transmit them to the processing unit 500 through the electrical connections located in the arms 600. The amplifier 350 will include noise filters and other signal processing circuitry known in the art to send a clearer, stronger voltage signal to the processing unit 500. In the event that scintillator crystal is chosen for 300, then a layer of avalanche photodiodes (APDs) could be used in 350 to amplify and convert the secondary photons into electrical signals.

Figure 4:
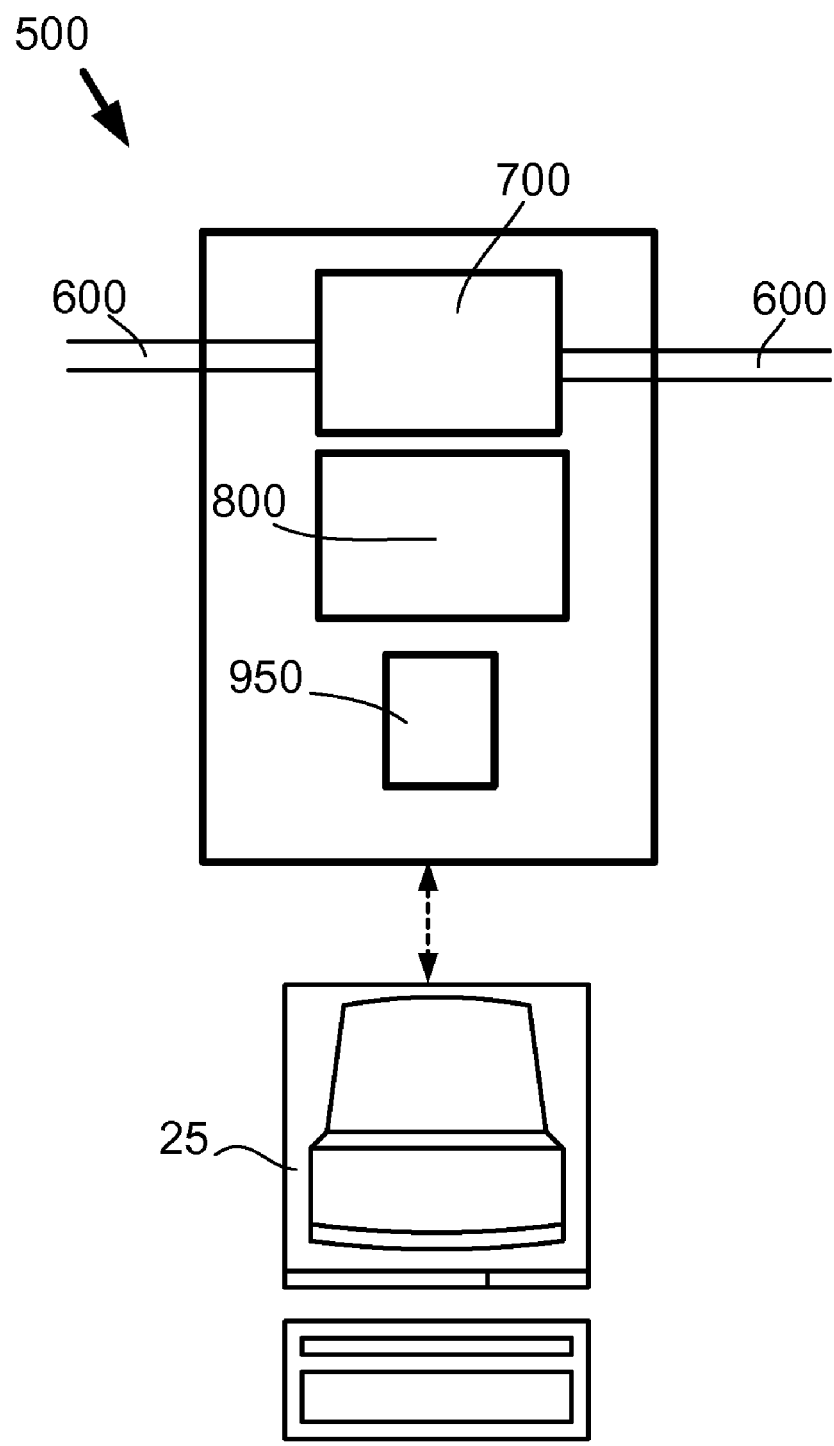
FIG. 4 is a schematic view of the processing unit used with the gamma ray counter of FIGS. 1 and 2.

FIG. 4 is a schematic view of the processing unit 500 used with the gamma ray counter 10 of FIGS. 1 and 2. Key components of the processing unit 500 include a controller 800, a coincidence counter 700, and a power supply 950. In preferred embodiments, the processing unit 500 is then connected to a personal computer 25 which can be used to input settings as well as display and record results. In alternative embodiments, the processing unit 500 can be a stand-alone device where the functions of a personal computer 25 are integrated in the processing unit 500 (e.g. include input controls, display unit, etc). Once the voltage output from both detectors 100*a* and 100*b* is received by the processing unit 500, the controller 800 (with its associated memory and software/firmware which contain the programming instructions to download and evaluate data recorded by the detectors 100*a* and 100*b*) deciphers the voltage output using a coincidence counter 700. The coincidence counter 700 counts coincident events within a user defined timing window. The user defined timing window is adjustable, but it is typically set to 7-10 nanoseconds which implies that each pair of photons which hit both detectors within this specified time are considered to represent an independent positron annihilation from the tracer within the body. The coincidence counter 700 will contain fast electronics which allow it to count large numbers of coincident events in the user defined timing window and then pass this information to the controller 800 and finally to the personal computer 25. In the preferred embodiment, the proposed total acquisition time for a hypoxia scan would be about 5 minutes. However, longer or shorter acquisition times can be specified by the user of the gamma ray counter 10, as needed. If the number of counts detected exceeds that found in a suitable nearby background (e.g. right lung), then the presence of the tracer is confirmed. For a hypoxia tracer with significant counts in the heart, this would signify the presence of an acute coronary syndrome and treatment to prevent further myocardial injury should be pursued. On the contrary, if the number of counts detected is similar to a suitable nearby background region, then hypoxia is absent from the heart, and workup of the patient can be halted and he/she discharged from the hospital with confidence. The coincidence counter 700 can be embodied as a separate counting circuit or simply run as software by the controller 800. In alternative embodiments, the detectors 100*a* and 100*b* can also be used in a singles mode if the tracer is a single photon emitter, and then total events (not necessarily coincident) will be counted by 700.

Control of the detectors 100*a* and 100*b* will be administered by the controller 800 (i.e. coincidence vs. singles mode). The processing unit 500 will also contain switches for turning the power supply 950 of the unit on and off, where the power switch can be activated directly on the processing unit 500 or sent as instructions from the personal computer 25. In preferred embodiments, the power supply will be designed to run off of 110 VAC, but alternatively other sources of power can be used including batteries, different voltages, power generator, etc. As described earlier, the attached personal computer 25 will provide a user interface for control of the detectors and counting circuit, as well as display the results of the gamma ray counter 10 on the monitor of the personal computer 25. Although in preferred embodiments, the personal computer 25 may simply interpret the result to indicate a yes/no or green/red type answer, additional information can also be provided. Actual count values received may be available to the physician to confirm the diagnosis. Specially designed software can also be used to calibrate the detectors, download the data, create a data file, and display the data in various formats including charts, forms, reports, graphs, tables, lists, and the like. The personal computer 25 can have an attached printer (not shown) or be networked to another printer or hospital server to print out these results. The personal computer 25 will also generally include the capability to record and store data as it is received from the detectors 100*a* and 100*b*, and includes either a data port (not shown) or wireless transmitter and/or receiver (also not shown) for transferring data to and/or from processing unit 500 as well as to other networked/connected devices (e.g. Bluetooth, PDA, etc.).

In alternative embodiments, the processing unit 500 may also include alarms or error warnings to notify the technologist or other operator of the gamma ray detector 10 if something is not properly working or the test was not being properly performed. In further alternatives, the display on the computer 25 may list each step needed in preparing the equipment, and/or may request a positive affirmation of each step by the operator before the test can be conducted.

Although the above description described the core concepts of the gamma ray counter 10 in the preferred embodiments, many modifications can be made to the above described device to add additional functionality or simply perform the described method using alternative steps.

In an alternative embodiment, the gamma ray counter 10 can be modified to act as an imaging device. Modifications that would need to be made include: pixilation of the semiconductor detectors (into 1 mm×1 mm×1 cm elements), independent amplification electronics for each pixel, a program on the PC 25 to acquire the coincident events in a listmode format with position and time stamp for each event, a reconstruction algorithm (iterative based on maximum likelihood estimation) on the PC 25, and a rotating chair for the patient, so that each detector can be swept through a 180 degree arc. Also, the possibility of mounting a transmission line source or transmission X-ray source on one detector head exists, so as to obtain an attenuation map on the opposite detector head, and then subsequently perform attenuation correction in post-processing of the image.

In still further embodiments, future tracers can be used with this gamma ray detector 10 to detect additional disease states. For example, there are new tracers that are still being developed based on specific binding to receptors, either through the synthesis of novel peptides or through antibody tagging. If, for example, a specific tracer is found for breast cancer (say based on the HER2/neu receptor) or for prostate cancer (based on prostate specific membrane antigen, etc.), then the mere presence or absence of radioactivity as determined by this gamma ray counter 10 will yield important diagnostic information. If a similar custom tracer is made for detecting a specific characteristic of colon cancer (based on dysplasia of adenomatous polyps), then this counter 10 could be used for early diagnosis of colorectal cancer. If a tracer can be fabricated specific for ovarian cancer (utilizing a reporter gene which is only transcribed during transcription of lysophosphatidic acid (LPA), thought by some to be more reliable than the CA-125 marker), then this gamma counter 10 could potentially be used as a screening device for ovarian cancer. At this time the mortality of ovarian cancer is very high, due to the advanced stage of the disease by the time it is detected.

Therefore, while the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of detecting a disease state in a targeted organ using nuclear medicine techniques comprising:
   administering an amount of positron emitting radiotracer with specific uptake for diseased portions of the targeted organ;
   operating a gamma ray counter with two separate gamma ray detectors for detecting 511 keV photons emitted from the positron emitting radiotracer;
   placing the at least two separate gamma ray detectors opposite each other over a location of the targeted organ;
   counting a number of 511 keV photons emitted from the location; and
   determining the presence of a disease state in the targeted organ based primarily on whether the number of 511 keV photons counted by the gamma ray counter exceeds a threshold.

2. The method of claim 1, wherein the targeted organ is the heart and the disease state is an acute coronary syndrome that can lead to a myocardial infarction.

3. The method of claim 2, wherein the positron emitting radiotracer is a hypoxic tracer.

4. The method of claim 2, wherein the positron emitting radiotracer indicates the presence of hypoxic myocardium.

5. The method of claim 2, wherein the positron emitting radiotracer is a special class of copper containing thiosemicarbazone ($^{62}$Cu-ATSM).

6. The method of claim 2, wherein the positron emitting radiotracer is a special class of 2-nitroimidazole derivatives with specific uptake for hypoxic tissue.

7. The method of claim 1, wherein the two separate gamma ray detectors are placed in front and back of the targeted organ and used in conjunction with a coincidence counter to detect the presence or absence of the disease state in the targeted organ.

8. The method of claim 1, wherein the two gamma ray detectors comprise a semiconductor material capable of converting gamma rays to an electrical signal.

9. The method of claim 8, wherein the semiconductor material is Cadmium-Zinc-Telluride (CZT) or Cadmium Telluride (CdTe).

10. The method of claim 1, wherein the gamma ray counter provides a yes or no answer on whether the disease state exists in the targeted organ within five minutes of activating the gamma ray counter.

11. The method of claim 1, wherein the gamma ray counter is portable.

12. The method of claim 1, wherein the gamma ray counter is connected to a computer which is used to input settings and display results of the gamma ray counter.

13. The method of claim 1, wherein the amount of positron emitting radiotracer administered is less than or equal to 5 mCi.

14. The method of claim 1, wherein the step of placing two gamma ray detectors over the location of the targeted organ further comprises using flexible arms comprised of a segmented flexible material to position and hold the two gamma ray detectors in place.

15. A system for detecting a disease state in a targeted organ using nuclear medicine techniques comprising:
   means for administering an amount of positron emitting radiotracer with specific uptake for diseased portions of the targeted organ;
   means for operating a gamma ray counter with two separate gamma ray detectors for detecting 511 keV photons emitted from the positron emitting radiotracer;
   means for placing the two separate gamma ray detectors opposite each other over a location of the targeted organ;
   means for counting a number of 511 keV photons emitted from the location; and
   means for determining if the presence of a disease state in the targeted organ based primarily on whether the number of 511 keV photons counted by the gamma ray counter exceeds a threshold.

16. The system of claim 15, wherein the targeted organ is the heart and the disease state is an acute coronary syndrome that can lead to a myocardial infarction.

17. The system of claim 16, wherein the positron emitting radiotracer is a hypoxic tracer.

18. The system of claim 16, wherein the positron emitting radiotracer indicates the presence of hypoxic myocardium.

19. The system of claim 16, wherein the positron emitting radiotracer is a special class of copper containing thiosemicarbazone ($^{62}$Cu-ATSM).

20. The system of claim 16, wherein the positron emitting radiotracer is a special class of 2-nitroimidazole derivatives with specific uptake for hypoxic tissue.

21. The system of claim 15, wherein the two separate gamma ray detectors are configured to be placed in front and back of the targeted organ and used in conjunction with a coincidence counter to detect the presence or absence of the disease state in the targeted organ.

22. The system of claim 15, wherein the two gamma ray detectors comprise a semiconductor material capable of converting gamma rays to an electrical signal.

23. The system of claim 22, wherein the semiconductor material is Cadmium-Zinc-Telluride (CZT) or Cadmium Telluride (CdTe).

24. The system of claim 15, wherein the gamma ray counter is configured to provide a yes or no answer on whether the disease state exists in the targeted organ within five minutes of activating the gamma ray counter.

25. The system of claim 15, wherein the gamma ray counter is portable.

26. The system of claim 15, wherein the gamma ray counter is connected to a computer which is used to input settings and display results of the gamma ray counter.

27. The system of claim 15, wherein the amount of positron emitting radiotracer administered is less than or equal to 5 mCi.

28. The system of claim 15, wherein the means of placing at least two gamma ray detectors over the location of the targeted organ further comprises flexible arms comprised of a segmented flexible material to position and hold the two gamma ray detectors in place.

29. A system for detecting acute coronary syndromes in the heart using nuclear medicine techniques comprising:
   a positron emitting hypoxia radiotracer;
   a gamma ray counter configured to count 511 keV rays emitted by the positron emitting hypoxia radiotracer from the heart;
   wherein the gamma ray counter comprises of two separate gamma ray detectors configured to be placed in front and back of the heart and a coincidence counter configured to detect the presence or absence of hypoxic myocardium based primarily on a number of coincident 511 keV photons counted exceeding a threshold.

* * * * *